(12) United States Patent
Motai et al.

(10) Patent No.: US 10,792,030 B2
(45) Date of Patent: Oct. 6, 2020

(54) SUTURING DEVICE

(71) Applicant: OLYMPUS CORPORATION, Hachioji-shi, Tokyo (JP)

(72) Inventors: Kosuke Motai, Hidaka (JP); Tetsuyuki Sakamoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 266 days.

(21) Appl. No.: 15/886,348

(22) Filed: Feb. 1, 2018

(65) Prior Publication Data

US 2018/0153539 A1 Jun. 7, 2018

Related U.S. Application Data

(63) Continuation of application No. PCT/JP2016/066870, filed on Jun. 7, 2016.

(30) Foreign Application Priority Data

Aug. 4, 2015 (JP) .................................. 2015-153844

(51) Int. Cl.
*A61B 17/04* (2006.01)
*A61B 17/00* (2006.01)

(52) U.S. Cl.
CPC .......... *A61B 17/0469* (2013.01); *A61B 17/04* (2013.01); *A61B 17/0401* (2013.01);
(Continued)

(58) Field of Classification Search
CPC . A61B 17/04; A61B 17/0469; A61B 17/0401; A61B 17/0485
See application file for complete search history.

(56) References Cited

U.S. PATENT DOCUMENTS 7,235,086 B2 * 6/2007 Sauer .................. A61B 1/0014
606/139
9,414,837 B2 * 8/2016 Oba .................. A61B 17/0487
(Continued)

FOREIGN PATENT DOCUMENTS

EP          1859743 A1   11/2007
JP       H09-098976 A    4/1997
(Continued)

OTHER PUBLICATIONS

Aug. 9, 2016 Search Report issued in International Patent Application No. PCT/JP2016/066870.
(Continued)

*Primary Examiner* — Julie A Szpira
(74) *Attorney, Agent, or Firm* — Oliff PLC (57) ABSTRACT

A device suturing device includes a flexbile tubular insertion portion; a suturing portion disposed at a distal end portion thereof holding a tubular anchor through which a suture thread is insertable; an operation portion disposed at a proximal end portion of the insertion portion; and a suture thread grasping portion inserted through the insertion portion and insertable through the anchor, wherein the suturing portion includes an installation surface on which the anchor is held; a pressing member including a convex portion being arranged to face the installation surface for pressing the anchor; and a driver operating the pressing member via the operation portion, wherein a concave portion is formed on the installation surface into which the convex portion is enterable, and the anchor is sandwiched between the concave portion and the convex portion to be swaged and deformed such that the suture thread is fixed to the anchor.

16 Claims, 6 Drawing Sheets

(52) U.S. Cl.
CPC ...... *A61B 17/0485* (2013.01); *A61B 17/0482* (2013.01); *A61B 2017/00663* (2013.01); *A61B 2017/0496* (2013.01)

(56) References Cited

U.S. PATENT DOCUMENTS

| | | | |
|---|---|---|---|
| 2002/0107530 A1 | 8/2002 | Sauer et al. | |
| 2003/0204205 A1* | 10/2003 | Sauer | A61B 1/0014 606/232 |
| 2005/0119671 A1 | 6/2005 | Reydel et al. | |
| 2005/0251207 A1* | 11/2005 | Flores | A61B 17/10 606/232 |
| 2005/0251210 A1* | 11/2005 | Westra | A61B 17/0401 606/232 |
| 2007/0073320 A1 | 3/2007 | Mikkaichi et al. | |
| 2010/0106166 A1* | 4/2010 | Cropper | A61B 17/0057 606/139 |
| 2011/0251641 A1* | 10/2011 | Sauer | A61B 17/0487 606/230 |
| 2015/0142021 A1* | 5/2015 | Smith | A61B 17/0467 606/148 |

FOREIGN PATENT DOCUMENTS

| | | |
|---|---|---|
| JP | 2002-540834 A | 12/2002 |
| JP | 2012-024607 A | 2/2012 |
| WO | 00/59383 A1 | 10/2000 |
| WO | 2006/098155 A1 | 9/2006 |
| WO | 2015/074040 A1 | 5/2015 |

OTHER PUBLICATIONS

Abreu, Sidney C. et al. "Use of Titanium Knot Placement Device (TK-5) To Secure Dorsal Vein Complex During Laparoscopic Radical Prostatectomy And Cystoprostatectomy". Urology, vol. 67, No. 1, p. 190-194, 2006.

Apr. 17, 2019 Extended European Search Report issued in European Patent Application No. 16832605.6.

* cited by examiner

SUTURING DEVICE

This application is a continuation application based on a PCT International Application No. PCT/JP2016/066870, filed on Jun. 7, 2016, whose priority is claimed on Japanese Patent Application No. 2015-153844, filed on Aug. 4, 2015. The contents of both the PCT International Application and the Japanese Patent Application are incorporated herein by reference.

BACKGROUND OF THE INVENTION

Field of the Invention

The present invention relates to a medical suturing device.

Description of Related Art

Conventionally, various procedures are performed by using a flexible endoscope which is inserted luminal organs such as the gastrointestinal tract and the like. Generally, such procedures are performed by inserting an endoscopic treatment device through a channel formed in an insertion portion of the endoscope and then protruding a distal end of the treatment device out of a distal end of the insertion portion of the endoscope.

Suturing procedures using a suture thread are regarded as a difficult procedure. A series of suturing procedures include an operation of making the suture thread through a tissue, and an operation of tying a knot on the suture thread for continuing applying a predetermined tension on the tissue. The latter operation is considered to be more difficult and it is not easy to be performed using the treatment device.

Instead of tying the knot, a method of fixing a suture fastener that is different from the suture thread to the suture thread in order to achieve the same function of the knot is proposed. A medical suturing apparatus disclosed in Japanese Unexamined Patent Application, First Publication No. H9-98976 is regarded as one of such suturing devices.

SUMMARY OF THE INVENTION

According to a first aspect of the present invention, a suturing device includes a tubular insertion portion having flexibility; a suturing portion disposed at a distal end portion of the insertion portion, the suturing portion holding a tubular anchor through which a suture thread is insertable; an operation portion disposed at a proximal end portion of the insertion portion; and a suture thread grasping portion inserted through the insertion portion, the suture thread grasping portion being configured to be insertable through the anchor, wherein the suturing portion includes an installation surface on which the anchor is held; a pressing member including a convex portion for pressing the anchor, the convex portion being arranged to face the installation surface; and a driver configured to operate the pressing member via the operation portion, wherein a concave portion is formed on the installation surface into which the convex portion is enterable, and wherein the anchor is sandwiched between the concave portion and the convex portion to be swaged and deformed such that the suture thread is fixed to the anchor.

According to a second aspect of the present invention, in the suturing device according to the first aspect, the convex portion may extend in one direction, and a dimension in a projecting direction of the convex portion may be larger than an external diameter of the anchor.

According to a third aspect of the present invention, in the suturing device according to the first aspect, the driver may include an operation member connected to the operation portion, and the driver may be driven by pulling the operation member with the operation portion.

According to a fourth aspect of the present invention, in the suturing device according to the first aspect, the pressing member may include a penetrating portion through which the suture thread grasping portion is insertable, and the pressing member may be configured such that an internal cavity of the anchor and the penetrating portion may be positioned on a straight line in an initial state before the driver is driven.

According to a fifth aspect of the present invention, a suturing device includes a tubular insertion portion having flexibility; a suturing portion disposed at a distal end portion of the insertion portion, the suturing portion holding a tubular anchor through which a suture thread is insertable; an operation portion disposed at a proximal end portion of the insertion portion; and a suture thread grasping portion inserted through the insertion portion, the suture thread grasping portion being configured to be insertable through the anchor, wherein the suturing portion includes an installation surface on which the anchor is held; a pressing member including a convex portion for pressing the anchor, the convex portion being arranged to face the installation surface; and a driver configured to operate the pressing member via the operation portion, wherein the drive includes an operation member connected to the operation portion, the driver being driven by pulling the operation member with the operation portion, and wherein the anchor is sandwiched between the installation surface and the convex portion to be pressed, and thus the anchor is deformed to a substantial V shape by driving the driver.

According to a sixth aspect of the present invention, in the suturing device according to the fifth aspect, the convex portion may extend in one direction, and a dimension in a projecting direction of the convex portion may be larger than an external diameter of the anchor, and the installation surface may include a concave portion into which the convex portion is enterable.

According to a seventh aspect of the present invention, in the suturing device according to the fifth aspect, the pressing member may include a penetrating portion through which the suture thread grasping portion is insertable, and the pressing member may be configured such that an internal cavity of the anchor and the penetrating portion are positioned on a straight line in an initial state before the driver is driven.

According to an eighth aspect of the present invention, a suturing device includes a tubular insertion portion having flexibility; a suturing portion disposed at a distal end portion of the insertion portion, the suturing portion holding a tubular anchor through which a suture thread is insertable; an operation portion disposed at a proximal end portion of the insertion portion; and a suture thread grasping portion inserted through the insertion portion, the suture thread grasping portion being configured to be insertable through the anchor, wherein the suturing portion includes an installation surface on which the anchor is held; a pressing member including a convex portion for pressing the anchor, the convex portion being arranged to face the installation surface; and a driver configured to operate the pressing member via the operation portion, wherein the pressing member includes a penetrating portion through which the suture thread grasping portion is insertable and the pressing member is configured such that an internal cavity of the anchor and the penetrating portion are positioned on a straight line in an initial state before the driver is driven, and wherein the anchor is sandwiched between the installation surface and the convex portion to be pressed, and thus the anchor is deformed to a substantial V shape by driving the driver.

According to a ninth aspect of the present invention, in the suturing device according to the eighth aspect, the convex portion may extend in one direction, a dimension in a projecting direction of the convex portion may be larger than an external diameter of the anchor, and the installation surface may include a concave portion into which the convex portion is enterable.

According to a tenth aspect of the present invention, in the suturing device according to the eighth aspect, the drive may include an operation member connected to the operation portion, and the driver may be driven by pulling the operation member with the operation portion.

DETAILED DESCRIPTION OF THE INVENTION

First Embodiment

Figure 1:
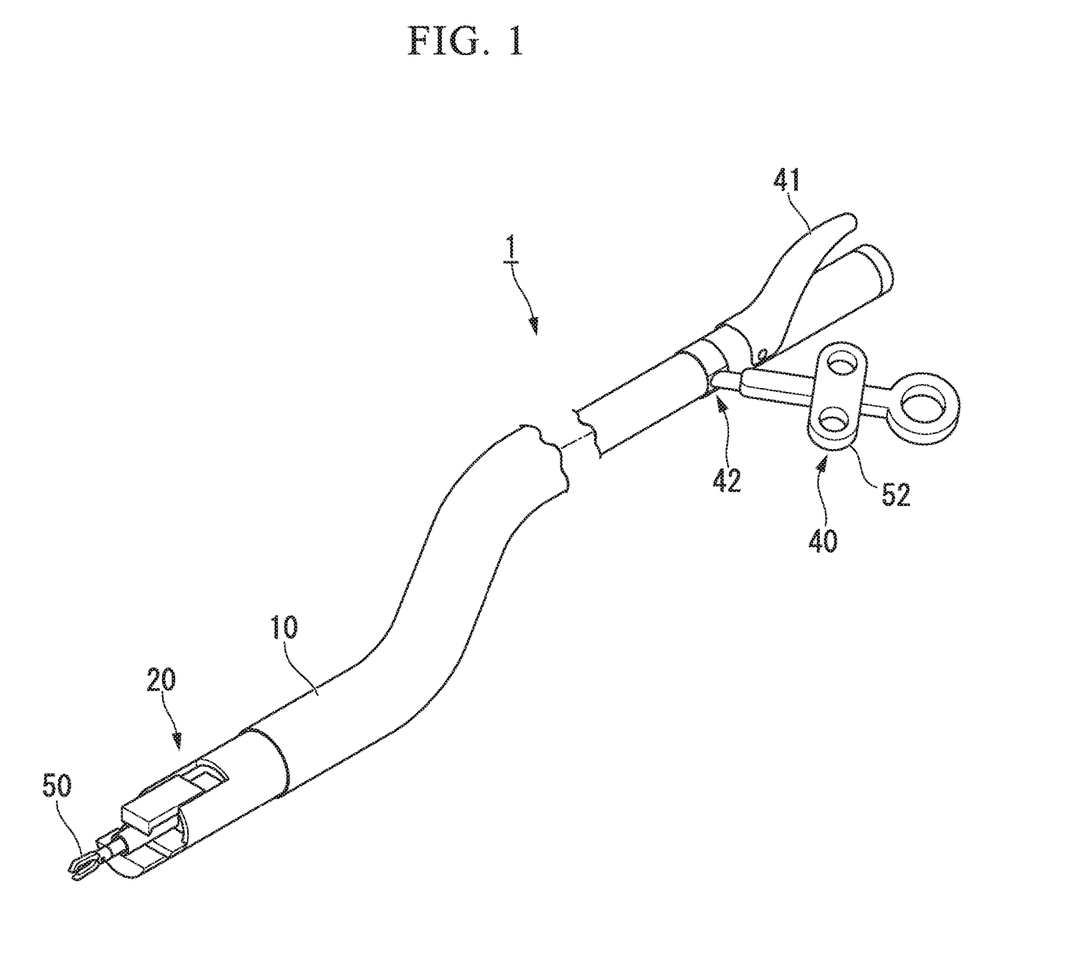
FIG. 1 is an oblique view showing an overall configuration of a suturing device according to a first embodiment of the present invention.

A first embodiment of the present invention will be described with reference to FIGS. 1 to 8. FIG. 1 is an oblique view showing an overall configuration of a suturing device 1 according to the present embodiment. The suturing device 1 includes an elongated insertion portion 10 with flexibility, a suturing portion 20 disposed at a distal portion of the insertion portion 10, an operation portion 40 disposed at a proximal end portion of the insertion portion 10, and a grasping forceps (a suture thread grasping portion) 50 inserted through the insertion portion 10.

The insertion portion 10 is formed from a coil or a resin and the like, and the insertion portion 10 is formed in a tubular shape. The insertion portion 10 has flexibility so that the insertion portion can follow the deformation of a channel of a flexible endoscope being used. When the suturing portion 20 is being driven (described below), a force of compression is applied to the insertion portion 10 along a direction of an axis line. Accordingly, the insertion portion 10 is preferred to have compression resistance by being configured using a coil or the like which is formed from metal wires.

Figure 2:
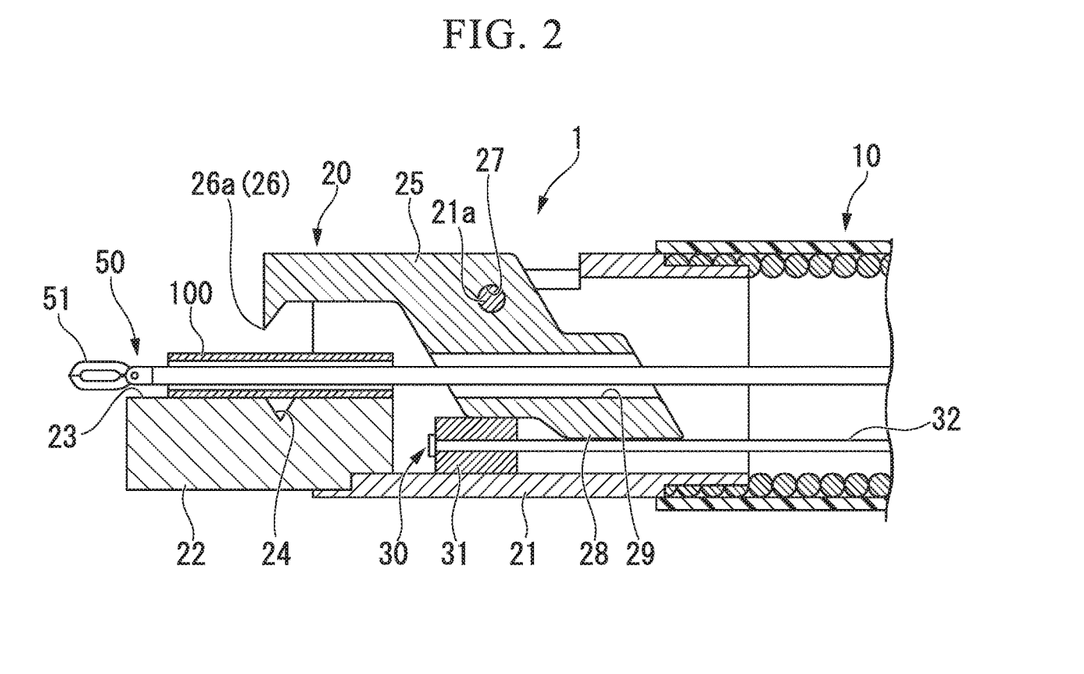
FIG. 2 is a cross section view showing a suturing portion of the suturing device according to the first embodiment of the present invention.

FIG. 2 is a cross section view of the suturing portion 20. The suturing portion 20 includes a tubular base body 21, a pressing stage 22 attached to the base body 21, a swaging member (a pressing member) 25 rotatably supported by the base body 21, and a driver 30 for driving the swaging member 25.

The pressing stage 22 includes an installation surface 23 on which a pipe (an anchor) 100 is installed, the pipe 100 being fixed to the suture thread in a state in which the suture thread is inserted through. A V-shaped groove (a concave portion) 24 is formed on the installation surface 23 and is extended in a direction orthogonal to a direction of an axis line of the base body 21.

The swaging member 25 includes a convex portion 26 disposed at a distal end portion thereof, a through hole 27 disposed at a middle portion thereof, and a driving projection 28 disposed at a proximal end side thereof. The swaging member is supported by the base body 21 and the pressing stage 22 while being relatively rotatable to the base body 21 and the pressing stage 22 since a rotation axis 21a disposed at the based boy 21 is inserted through the through hole 27. The convex portion 26 includes a ridgeline 26a extending in one direction. When the swaging member 25 is rotated about the rotation axis 21a as a rotary center so that the convex portion 26 approaches the V-shape groove 24, the direction in which the ridgeline 26a extends and the direction in which the V-shape groove 24 extends substantially coincide with each other, and the ridgeline 26a can enter the V-shape groove 24.

In the swaging member 25, a shaft hole (a penetrating portion) 29 is formed on an opposite side of the convex portion 26 with respect to the through hole 27, and the shaft hole 29 extends in a direction orthogonal to the through hole 27. The shaft hole 29 has openings at two ends thereof, and the shaft hole 29 has an internal diameter so that the grasping forceps 50 can be inserted through the shaft hole 29. The driving projection 28 projects at a position farther than the position of the shaft hole 29 with respect to the through hole 27.

The driver 30 includes a rigid main body 31, and a wire (an operation member) 32 for driving the main body. The main body 31 has a suitable rigidness so that the swaging member 25 can be rotated when the main body gets over the driving projection (described below). The wire 32 extends to the operation portion 40 via the inside of the insertion portion 10.

As shown in FIG. 1, the operation portion 40 includes a handle 41 for driving the driver 30, and a forceps port 42 into which the grasping forceps 50 is inserted. The handle 41 is connected by the wire 32, and the main body 31 of the driver 30 can be moved in a direction approaching the operation portion 40 when the handle 42 is held.

The grasping forceps 50 includes a grasping portion 51 formed from a pair of jaws, and a slider 52 for opening and closing the grasping portion 51. A basic configuration of the grasping portion 50 is known to be the same with a configuration of a general grasping forceps used by being inserted through a flexible endoscope. The grasping forceps 50 has a dimension of being insertable into the forceps port 42, the shaft hole 29 of the swaging member 25, and the pipe 100, and the grasping forceps 50 is configured to be smaller than the general grasping forceps.

An operation of the suturing device 1 having the configuration described above according to the present embodiment when being used will be described below. Firstly, the surgeon inserts a flexible endoscope into the luminal organs of a patient, and the surgeon performs threading procedures of inserting a suturing needle through the target tissue to make the suture thread through the target tissue by using a suturing unit configured by attaching the suturing needle to an end of the suture thread. The threading procedures can be performed using a known suturing apparatus used by inserting through the flexible endoscope. A suturing apparatus with a configuration of delivering and receiving the suturing needle between a pair of jaws, and a suturing apparatus with a configuration of driving a bent needle can be regarded as examples of the known suturing apparatus.

After the threading is finished, the surgeon separates the suturing needle from the suture thread and then removes the suturing apparatus used during the threading from the flexible endoscope. Subsequently, the surgeon installs the pipe 100 on the installation surface 23 of the pressing stage 22. The pipe 100 preferably has a radial dimension less than the ridgeline 26a and the V-shape groove 24. A material which is plastic deformable, such as a metal or a resin and the like, can be adopted as the material of the pipe, and a material with a high-level biocompatibility such as a titanium or a stainless steel and the like is more preferable. The pipe 100 is preferably installed in a manner that a direction of an axis line of the pipe 100 is orthogonal to the direction in which the V-shape groove 24 extends.

After the installation of the pipe 100, the surgeon inserts the suturing device 1 into the channel of the flexible endoscope. Subsequently, the surgeon inserts the grasping forceps 50 into the forceps port 42. The grasping forceps 50 may be inserted into the forceps port 42 before the insertion of the suturing device 1 into the flexible endoscope.

As shown in FIG. 2, in an initial state of the suturing device 1 before being driven by the driver 30, the shaft hole 29 of the swaging member 25 and an internal cavity of the pipe 100 have a positional relationship of being coaxially positioned (a positional relationship of being substantially coaxially positioned is included, and so forth) and are arranged in a same straight line. Accordingly, the grasping forceps 50 inserted into the forceps port 42 can be easily inserted through the shaft hole 29 and the pipe 100 to cause the grasping portion 51 to project from the pipe 100.

Figure 3:
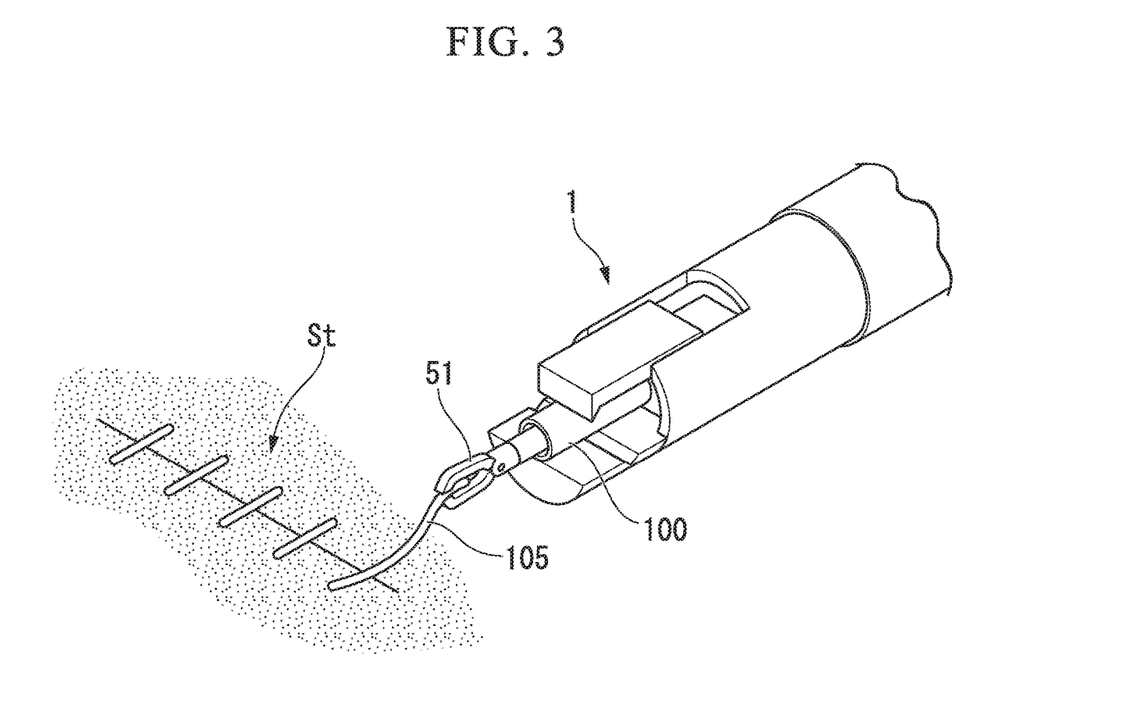
FIG. 3 is a view showing an operation of the suturing device being used according to the first embodiment of the present invention.
Figure 4:
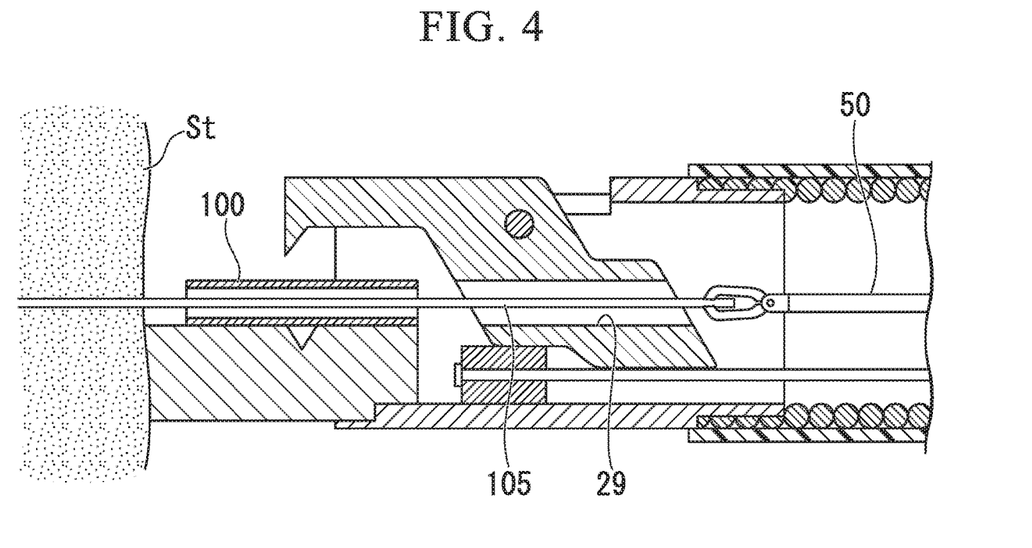
FIG. 4 is a view showing another operation of the suturing device being used according to the first embodiment of the present invention.

The surgeon moves the suturing device 1 in a state in which the grasping portion 51 projects from the pipe 100 to approach a target tissue St, and as shown in FIG. 3, the surgeon uses the grasping portion 51 to grasp an end portion of the suture thread 105 which is placed in the target tissue St. Subsequently, the surgeon pulls the grasping forceps 50 proximally to the hand side to remove the grasping forceps 50 from the pipe 100 and the shaft hole 29. As shown in FIG. 4, according to such an operation, the suture thread 105 is inserted through the pipe 100 and the shaft hole 29.

Next, the surgeon abuts the distal end of the suturing device 1 with the target tissue St while pulling the grasping forceps 50 which grasps the suture thread 105 proximally to the hand side. According to this operation, an incision of the target tissue St which should be closed by the suturing procedures is closed, and at the same time a tension applied to the target tissue St by the suture thread 105 is suitably adjusted to a desired amount.

Figure 5:
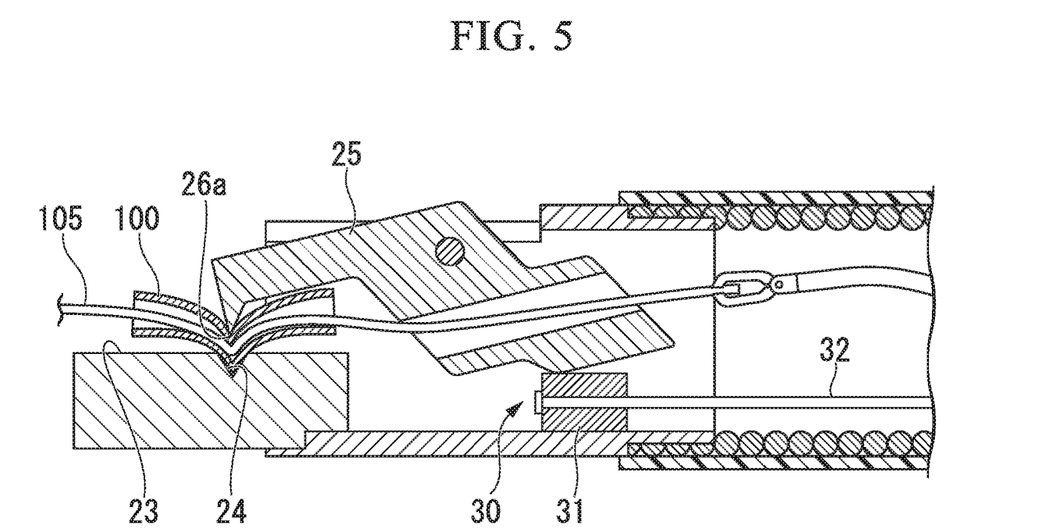
FIG. 5 is a view showing another operation of the suturing device being used according to the first embodiment of the present invention.

Subsequently, the surgeon keeps the tension and holds the handle 41 to drive the driver 30. When the handle 41 is held, the wire 32 is proximally pulled to the hand side and the main body 31 moves in a direction approaching the operation portion 40, thus the main body 31 contacts with the driving projection 28 of the swaging member 25. When the wire 32 is further pulled, the main body 31 presses the driving projection 28. As a result, the swaging member 25 rotates about the rotation axis 21a as the rotary center, and the convex portion 26 directed to the installation surface 23 approaches and contacts with the pipe 100. According to this operation, the pipe 100 is sandwiched between the convex portion 26 and the installation surface 23. Further, as shown in FIG. 5, a pressing force is applied to the pipe 100 from the ridgeline 26a so that the pipe 100 is folded along a portion with which the ridgeline 26a contacts regraded as a fold line. The pipe 100 is deformed and a part of the folded pipe 100 enters the V-groove 24.

Accordingly, the pipe 100 is swaged so that the suture thread 105 inserted through the pipe 100 is in contact with the internal surface of the pipe 100 and the pipe 100 is fixed to the suture thread 105.

Figure 6:
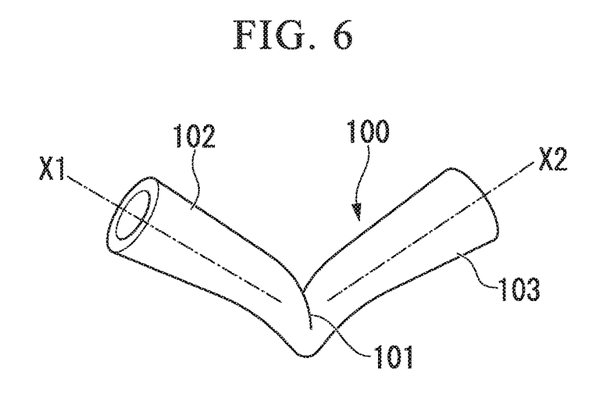
FIG. 6 is a view showing a deformed pipe.

FIG. 6 shows a view of the deformed pipe 100. The pipe 100 used to be a linear shape is swaged to be deformed into a substantial V-shape by being sandwiched between the pressing stage 22 and the swaging member 25 and being applied with a force from the convex portion 26, thus an angle is formed between an axis line X1 of a first region 102 positioned more distal than a folding line 101 with which the ridgeline contacts and an axis line X2 of a second region 103 positioned more proximal than the folding line 101, and the axis line X1 and the axis line X2 are nonparallel to each other.

Figure 7:
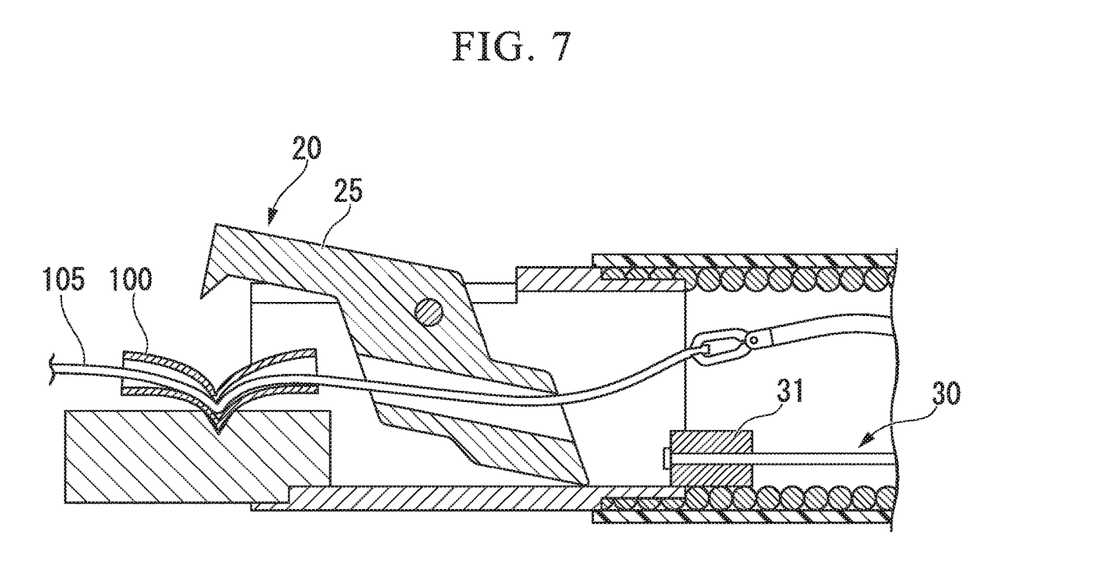
FIG. 7 is a view showing another operation of the suturing device being used according to the first embodiment of the present invention.

As shown in FIG. 7, when the wire 32 is further pulled, the main body 31 gets over the driving projection 28 which is moved due to the rotation of the swaging member 25, and the main body 31 moves to a position closer than that of the driving projection 28 with respect to the operation portion 40. In this state, since the rotation of the swaging member 25 is not restricted by the driver 30, when the suturing device 1 is retracted with respect to the target tissue St, both the pipe 100 and the suture thread 105 are separated from the suturing portion 20. Finally, the unnecessary suture projecting from the pipe 100 is cut off and a series of the procedures are finished.

Figure 8:
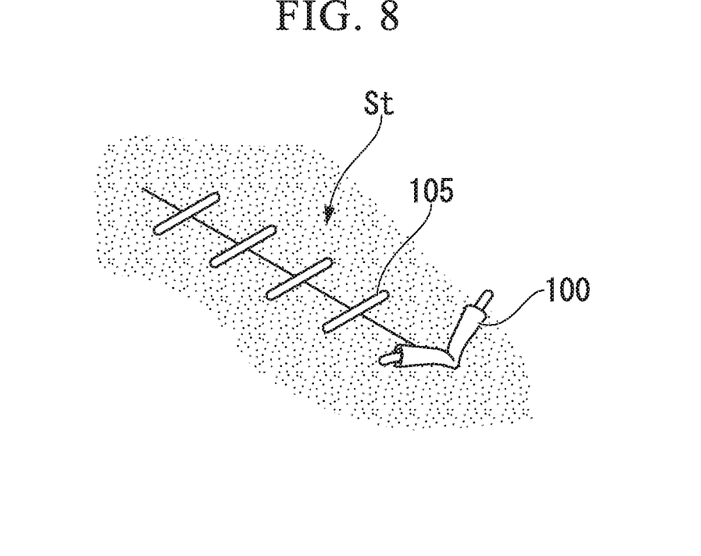
FIG. 8 is a view showing a target tissue when the suturing procedures are finished.

As shown in FIG. 8, since the pipe 100 fixed to the suture thread 105 cannot enter the target tissue St, as the same effects with the knot finally formed during the procedures of tying a surgeon's knot, the pipe 100 prevents the suture thread 105 placed at the target tissue St from loosening. As a result, the suture thread 105 is suitably kept at the target tissue St in a state of being applied with a desired tension.

As described above, according to the suturing device 1 according to the present embodiment, the pipe 100 inserted through by the suture thread 105 is swaged to be deformed into the substantial V-shape, such that the axis line X1 of the first region 102 and the axis line X2 of the second region 103 at the proximal side are nonparallel to each other, for fixing the suture thread 105 and the pipe 100 with each other. Accordingly, the suture thread 105 is bent to be a substantial V-shape inside the pipe 100 following the axis line X1 and axis line X2, and the suture thread 105 is pressed by an inwardly projecting part of the internal surface of the pipe 100 at the folded position of the pipe 100. As a result, a large friction is generated between the suture thread 105 and the pipe 100 for more definitely fixing the suture thread 105 and the pipe 100 with each other, comparing to a general swaging performed while keeping the linear shape of the pipe.

According to the suturing device 1, the surgeon without a high-level technique can also easily and definitely perform the procedures equivalent to the formation of a knot during the suturing procedures.

The V-shape groove 24 and the convex portion 26 are formed at the pressing stage 22 and the swaging member 25 which are configured to sandwich and deform the pipe 100, respectively. Accordingly, the part of the pipe 100 pressed by the convex portion 26 can be suitably deformed into the V-shape groove 24 like dropping into the V-shape groove 24.

Since the lengths of the V-shaped groove 24 and the convex portion 26 are larger than the external diameter of the pipe 100, the V-shaped groove 24 and the convex portion 26 can press the pipe 100 over the whole radial direction of the pipe 100, and thus the pipe 100 can be pressed and bent to be suitably deformed into the substantial V shape.

Further, the driver 30 for driving the swaging member 25 is driven by pulling the wire 32 connected to the operation portion 40. In a flexible treatment device, sine buckling and the like occurs easily when the operation member such as a wire and the like used for transmitting the operation force is pushed, it is not easy to suitably transmit the operation force by the pushing operation, however, the operation force can be suitably transmitted by the pulling operation.

As a result, even the insertion portion is configured with a flexible structure, the operation force generated for driving the swaging member 25 is enough to easily perform the suturing procedures. Such effects are made more remarkable by enhancing the compression resistance of the insertion portion 10.

The pipe 100 is arranged to be parallel to the longitudinal direction of the suturing device 1, thus the insertion of the grasping forceps 50 into the pipe 100 and the insertion of the suture thread 105 into the pipe 100 can be easily performed only by advancing and retracting the grasping forceps 50.

The swaging member 25 includes the shaft hole 29, and the pipe 100 and the shaft hole 29 have the positional relationship of being arranged in the same straight line in the initial state, thus it is easy to insert the grasping forceps 50 through the shaft hole 29 and the pipe 100 by only advancing the grasping forceps 50 inserted into the insertion portion 10.

According to the present embodiment, the arrangement of the pipe 100 held on the installation surface 23 is not limited. For example, the pipe 100 may be held by slightly pulling the driver 30 to the hand side to slightly sandwich the pipe 100 between the swaging member 25 and the pressing stage 22, and the pipe 100 may be temporarily held on the installation surface 23 using the adhesive agent and the like. The position of the pipe 100 on the installation surface 23 may be stabilized by arranging the pipe 100 in a shallow groove which is formed to be orthogonal to the V-shape groove 24 on the installation surface 23.

Besides the shape of the shaft hole 29 described above, the penetrating portion may be gutter-shaped that an internal surface of the penetrating portion is not continuous in a circumferential direction.

Next, a second embodiment of the present invention will be described with reference to FIGS. 9 and 10. A suturing device 151 according to the present embodiment includes a suturing portion which has a different configuration with that of the suturing device 1 according to the first embodiment. In the following description, it is to be noted that like reference numerals designate identical or corresponding components throughout the drawings and duplicate descriptions are omitted.

Figure 9:
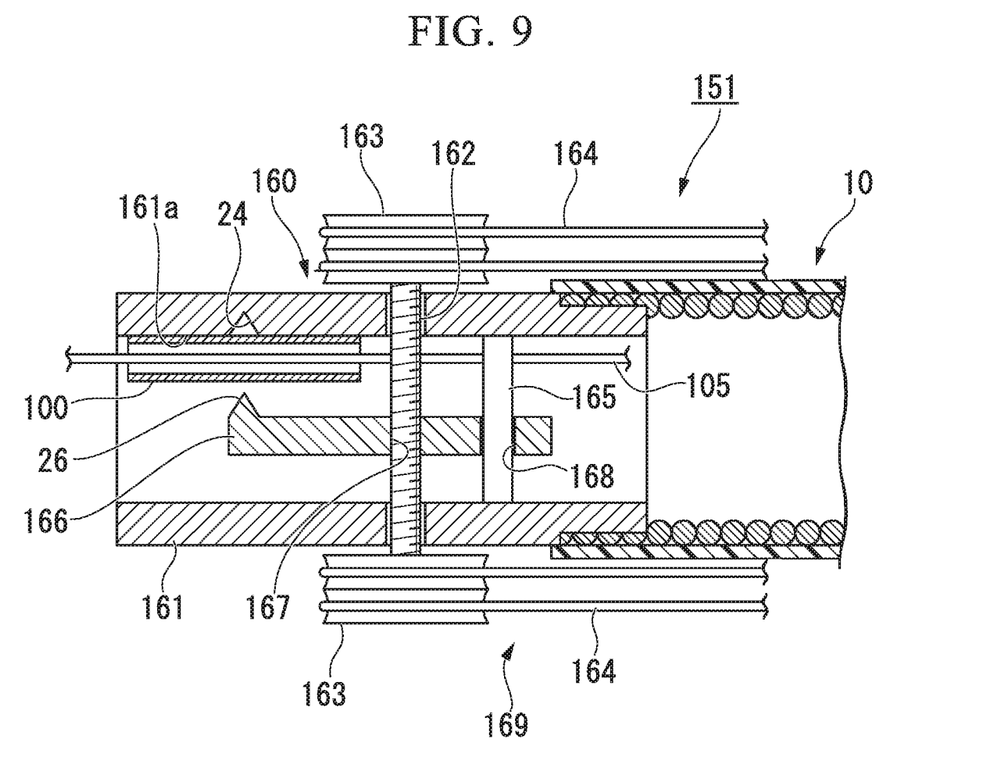
FIG. 9 is a cross section view showing a suturing portion of a suturing device according to a second embodiment of the present invention.

FIG. 9 is a cross section view showing a suturing portion 160 of the suturing device 151. In the suturing portion 160, a part of an internal surface of a tubular base body 161 is formed to be flat and is regarded as an installation surface 161a. A screw shaft 162 having a screw groove cut on an external surface thereof is configured to penetrate the base body 161. Two pulleys 163 are fixed to both two end portions of the screw shaft 162 projecting from the external surface of the base body 161, respectively, and a wire 164 is wound about each of the pulleys 163 wherein the wire 164 is circularly connected. The wire 164 is attached to an operation pulley (not shown) of an operation portion (not shown) along the insertion portion 10.

Inside the base body 161, a rod-shaped guide 165 is installed to be parallel to the screw shaft 162.

A swaging member 166 includes the same convex portion 26 according to the first embodiment. A first through hole 167 with a screw groove and a second through hole 168 without any screw groove are provided at a proximal side relative to the convex portion 26. The swaging member 166 is disposed inside the base body 161 in a manner such that the screw shaft 162 is inserted through the first through hole 167 by a screw fitting with the first through hole 167, and the guide 165 is inserted through the second through hole 168.

In the suturing portion 160, all of the screw shaft 162, the pulley 163, the wire 164, and the guide 165 corporately operate to realize the function as a driver 169.

When the suturing device 151 is used, the surgeon temporarily fixes the pipe 100 on the installation surface 161a by adhesive and the like, and performs the same procedures according to the first embodiment to insert the suture thread 105 through the pipe 100 using the grasping forceps 50 (not shown).

Next, the surgeon rotates the operation pulley in a predetermined direction to pull the wire 164. Due to the operation, both the pulley 163 and the screw shaft 162 rotate. At this time, since the guide 165 is inserted through the swaging member 166, the screw shaft 162 and the swaging member 166 rotate relatively with each other rather than rotating integrally. As a result, the swaging member 166 moves upwardly to approach the installation surface 161a due to the screw fitting. Eventually, the convex portion 26 contacts with the pipe 100, and the pipe 100 is pressed to be deformed into the substantial V-shape.

When the pipe 100 is deformed and fixed with respect to the suture thread 105, the surgeon rotates the operation pulley in an opposite direction such that the swaging member 166 moves downwardly. In such a state, the surgeon retracts the suturing device 151, and thus the pipe 100 is separated from the installation surface 161a.

According to the present embodiment, since the suturing device 151 is configured to drive the swaging member 165 by pulling the wire 164, as the same with the suturing device 1 according to the first embodiment, even the insertion portion has a flexible structure, the suturing procedures can be easily performed.

Figure 10:
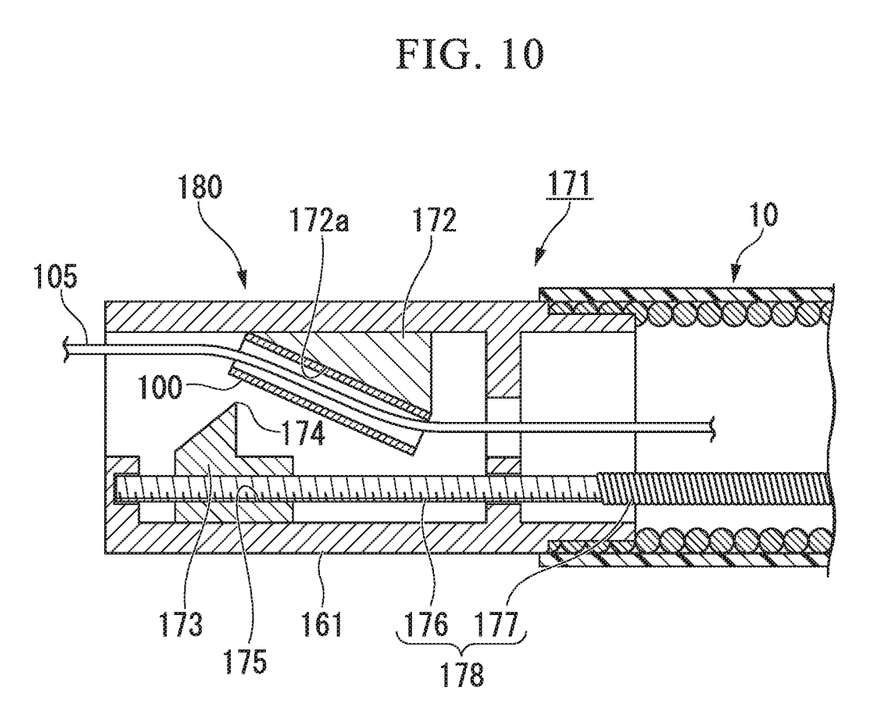
FIG. 10 is a cross section view showing a modification of the suturing device according to the second embodiment of the present invention.

FIG. 10 shows a modification of the present embodiment. FIG. 10 is a cross section view showing a suturing portion 180 of a suturing device 171 according to the present modification. A pressing stage 172 including an inclined surface 172a is installed inside the tubular base body 161. The inclined surface 172a functioning as the installation surface is directed to the distal end side of the suturing portion 180, and the pipe 100 is held on the inclined surface 172a by adhesive or engagement and the like.

The swaging member 173 including a convex portion 174 is configured to be more distal than the pressing stage 172 in a state in which the convex portion 174 is directed to the side of the inclined surface 172a. A screw shaft 176 is inserted through a through hole 175 formed in the swaging member 173, and the swaging member 173 and the screw shaft 176 are screw fitted with each other.

The screw shaft 176 extends parallely to an axis line of the base body 161. A proximal portion of the screw shaft 176 is connected to a distal end portion of a coil shaft 177 at a position relatively close to the base body 161 inside the insertion portion 10. The coil shaft 177 extends to an operation portion (not shown) through the inside of the insertion portion 10.

According to the suturing device 171 of the present modification, when the surgeon operates the operation portion to rotate the coil shaft 177 about the axis line thereof in a predetermined direction, the screw shaft 176 rotates about the axis line. As a result, the swaging member 173 relatively moves with respect to the screw shaft 176 and the convex portion 174 approaches the pipe 100 held by the pressing stage 172. Afterwards, the convex portion 174 contacts with the pipe 100 and presses the pipe 100 to deform the pipe 100 into the substantial V-shape.

The coil shaft 177 has flexibility and can suitably follow the bending and the meandering of the insertion portion 10.

According to the suturing device 171 according to the present modification, the same as the other embodiments, even the insertion portion has a flexible structure, and the suturing procedures can be easily performed.

Since the screw shaft 176 and the coil shaft 177 functioning as a driver 178 are disposed inside the insertion portion 10 and configured to be along the longitudinal direction of the insertion portion 10, the miniaturization of the suturing portion is easier compared with the suturing device 151 described above.

The embodiments of the invention have been described above with reference to the drawings, but specific structures of the invention are not limited to the embodiments and may include various modifications without departing from the scope of the invention.

For example, a concave portion may be formed on the inclined portion 172a of the suturing device 171 according to the present modification, and the concave portion disclosed in the other embodiments may be omitted.

Regarding the configuration of the concave portion, a groove formed with a curved bottom surface may be adopted instead of the V-shape groove in which the deepest portion extends linearly.

The embodiments of the invention have been described above with reference to the drawings, but specific structures of the invention are not limited to the embodiments and may include various modifications without departing from the scope of the invention. The invention is not limited to the above-mentioned embodiments and is limited only by the accompanying claims.

What is claimed is:

1. A suturing device, comprising:
a tubular insertion portion having flexibility;
a suturing portion disposed at a distal end portion of the insertion portion, the suturing portion holding a tubular anchor through which a suture thread is insertable;
an operation portion disposed at a proximal end portion of the insertion portion; and
a suture thread grasping portion inserted through the insertion portion, the suture thread grasping portion being configured to be insertable through the anchor, wherein:
the suturing portion includes:
an installation surface on which the anchor is held;
a pressing member including a convex portion for pressing the anchor, the convex portion (1) being arranged to face the installation surface and (2) forming a sharp edge facing the installation surface; and
a driver configured to operate the pressing member via the operation portion;
a concave portion is formed on the installation surface into which the convex portion is enterable; and
the anchor, the concave portion and the convex portion are configured such that the anchor is sandwiched between the concave portion and the convex portion to be swaged and deformed by movement of the convex portion towards the concave portion such that the suture thread is fixed to the anchor.

2. The suturing device according to claim 1, wherein the convex portion extends in a projecting direction toward the installation surface, and wherein a dimension in the projecting direction of the convex portion is larger than an external diameter of the anchor.

3. The suturing device according to claim 1, wherein the driver includes an operation member connected to the operation portion, and wherein the driver is driven by pulling the operation member with the operation portion.

4. The suturing device according to claim 1, wherein the pressing member includes a penetrating portion through which the suture thread grasping portion is insertable, and wherein the pressing member is configured such that an internal cavity of the anchor and the penetrating portion are positioned on a straight line in an initial state before the driver is driven.

5. The suturing device according to claim 1, wherein:
the anchor has a longitudinal axis; and
the sharp edge extends in a direction that intersects the longitudinal axis.

6. The suturing device according to claim 5, wherein the concave portion is a V-shaped groove in the installation surface.

7. A suturing device, comprising:
a tubular insertion portion having flexibility;
a suturing portion disposed at a distal end portion of the insertion portion, the suturing portion holding a tubular anchor through which a suture thread is insertable;
an operation portion disposed at a proximal end portion of the insertion portion; and
a suture thread grasping portion inserted through the insertion portion, the suture thread grasping portion being configured to be insertable through the anchor, wherein:
the suturing portion includes:
an installation surface on which the anchor is held;
a pressing member including a convex portion for pressing the anchor, the convex portion (1) being arranged to face the installation surface and (2) forming a sharp edge facing the installation surface; and a driver configured to operate the pressing member via the operation portion;

driver is operatively connected to the operation portion, the driver being driven by being pulled towards the operation portion by the operation portion; and the anchor, the installation surface and the convex portion are configured such that the anchor is sandwiched between the installation surface and the convex portion to be pressed, and thus the anchor is deformed to a substantial V shape by driving the driver.

8. The suturing device according to claim 7, wherein the convex portion extends in a projecting direction toward the installation surface and a dimension in the projecting direction of the convex portion is larger than an external diameter of the anchor, and wherein the installation surface includes a concave portion into which the convex portion is enterable.

9. The suturing device according to claim 7, wherein the pressing member includes a penetrating portion through which the suture thread grasping portion is insertable, and wherein the pressing member is configured such that an internal cavity of the anchor and the penetrating portion are positioned on a straight line in an initial state before the driver is driven.

10. The suturing device according to claim 7, wherein:

the anchor has a longitudinal axis; and the sharp edge extends in a direction that intersects the longitudinal axis.

11. The suturing device according to claim 10, wherein:

the installation surface includes a concave portion into which the convex portion is enterable; and the concave portion is a V-shaped groove in the installation surface.

12. A suturing device, comprising:

a tubular insertion portion having flexibility;

a suturing portion disposed at a distal end portion of the insertion portion, the suturing portion holding a tubular anchor through which a suture thread is insertable;

an operation portion disposed at a proximal end portion of the insertion portion; and a suture thread grasping portion inserted through the insertion portion, the suture thread grasping portion being configured to be insertable through the anchor, wherein:

the suturing portion includes:

an installation surface on which the anchor is held;

a pressing member including a convex portion for pressing the anchor, the convex portion (1) being arranged to face the installation surface and (2) forming a sharp edge facing the installation surface; and a driver configured to operate the pressing member via the operation portion;

the pressing member (1) includes a penetrating portion that extends a length of the pressing member and through which the suture thread grasping portion is insertable and (2) is configured such that an internal cavity of the anchor and the penetrating portion are positioned on a straight line in an initial state before the driver is driven; and the anchor, the installation surface and the convex portion are configured such that the anchor is sandwiched between the installation surface and the convex portion to be pressed, and thus the anchor is deformed to a substantial V shape by driving the driver.

13. The suturing device according to claim 12, wherein the convex portion extends in a projecting direction toward the installation surface, wherein a dimension in the projecting direction of the convex portion is larger than an external diameter of the anchor, and wherein the installation surface includes a concave portion into which the convex portion is enterable.

14. The suturing device according to claim 12, wherein the drive includes an operation member connected to the operation portion, and wherein the driver is driven by pulling the operation member with the operation portion.

15. The suturing device according to claim 12, wherein:

the anchor has a longitudinal axis; and the sharp edge extends in a direction that intersects the longitudinal axis.

16. The suturing device according to claim 15, the installation surface includes a concave portion into which the convex portion is enterable; and the concave portion is a V-shaped groove in the installation surface.

* * * * *